United States Patent [19]

Olsen et al.

[11] Patent Number: 5,030,763

[45] Date of Patent: Jul. 9, 1991

[54] PREPARATION OF ETHYLENEDIAMINE DINITRATE WITH USEFUL PARTICLE SIZE

[75] Inventors: Robert E. Olsen, Placerville; George D. Homer, Orangevale; James C. Barnard, Shingle Springs, all of Calif.

[73] Assignee: Aerojet-General Corporation, Folsom, Calif.

[21] Appl. No.: 479,556

[22] Filed: Feb. 13, 1990

[51] Int. Cl.$^5$ .................................. C07C 209/00
[52] U.S. Cl. ..................... 564/511; 149/92; 149/111; 564/498
[58] Field of Search ............ 564/497, 498, 511; 149/47, 62, 92, 110, 111

[56] References Cited

U.S. PATENT DOCUMENTS

| Re. 21,528 | 8/1940 | Fisk | 564/511 |
|---|---|---|---|
| 2,325,064 | 7/1942 | Lawrence | 149/47 |
| 2,739,981 | 3/1956 | Szabo et al. | 564/511 |
| 4,353,758 | 10/1982 | Akst | 149/109.6 |
| 4,539,430 | 9/1985 | Lee | 564/511 |
| 4,582,937 | 4/1986 | Hiraga et al. | 564/498 |

*Primary Examiner*—Glennon H. Hollrah
*Assistant Examiner*—Peter G. O'Sullivan
*Attorney, Agent, or Firm*—Townsend and Townsend

[57] ABSTRACT

A method of making ethylenediamine dinitrate comprising:
(a) reacting ethylenediamine with aqueous nitric acid to form ethylenediamine dinitrate solution; and
(b) adding said ethylenediamine dinitrate solution to a non-aqueous liquid, miscible with water in amounts of at least about 50 percent by weight, and in which ethylenediamine dinitrate is insoluble, to form solid ethylenediamine dinitrate with an average particle size of about 30 microns in diameter.

26 Claims, No Drawings

PREPARATION OF ETHYLENEDIAMINE DINITRATE WITH USEFUL PARTICLE SIZE

BACKGROUND OF THE INVENTION

This invention relates to ingredients for explosive compositions. In particular, this invention relates to an ingredient with a useful particle size and a safe method for its production.

Various ingredients are used in the formulation of explosive compositions. Ethylenediamine dinitrate (EDDN) is one such ingredient. In large scale production, it is currently prepared by the addition of concentrated nitric acid to a solution of ethylenediamine in cold methanol or ethanol, or by addition of concentrated nitric acid to a solution of ethylenediamine in a cold methanol/water or ethanol/water mixture. The ethylenediamine used in the process is well known in the art. For example, U.S. Pat. No. 4,353,758 to Akst, et al., at column 1, lines 10 through 12, discloses the use of ethylenediamine and nitric acid in a conventional process of producing EDDN.

A persistent problem with these procedures are the significant exotherms observed during the nitric acid addition. These exotherms promote the formation in the vapor phase of the volatile, highly hazardous methyl nitrate or ethyl nitrate by the reaction of methanol or ethanol with nitric acid. The likelihood of such a hazardous situation occurring increases in the event of a runaway reaction and also increases when production of EDDN is scaled up, as large quantities of the methyl and ethyl nitrate vapors can concentrate by condensing on cold process surfaces.

An additional problem of the above described manufacturing technique is that it produces crystalline EDDN with a large, 150 micron average particle size. This particle size is too large for many explosive applications, requiring grinding of the EDDN or similar operations before the material can be used, creating another hazardous situation.

SUMMARY OF THE INVENTION

It has now been discovered that a crystalline form of EDDN with a useful particle size may be formed using a safe, economical method.

One advantage of the present inventive method is the increased safety for industrial-scale production of EDDN. The process virtually eliminates the possibility of formation of volatile, hazardous methyl and ethyl nitrates.

A further advantage of this method is the particle size of EDDN produced by the method. The particle size is critical to successful utilization of many explosive ingredients in industry, where the explosives need to be shock insensitive during transportation and storage but able to be detonated by conventional methods when needed.

DESCRIPTION OF THE PREFERRED EMBODIMENT

EDDN with useful particle size is produced by the novel method comprising first neutralizing an aqueous solution of ethylenediamine with an acidic nitrate solution to form the EDDN in a solution which is substantially depleted in nitrate ion. The reaction may take place at any combination of temperature, pressure, and degree of agitation which does not result in substantial vapor generation or uncontrollable temperature rise during the reaction, and yet permits the reaction to proceed to completion within a reasonable and commercially useful period of time. The completeness of this reaction is determined by pH measurement.

The term "acidic nitrate solution" as used herein refers to an acidic solution containing nitrate ions. The acidic nitrate solution may be any solution which does not significantly alter the purity or yield of solid EDDN product, or result in additional separation steps to be performed. For convenience, nitric acid is used for explanatory purposes, but it is to be kept in mind that other acidic nitrate solutions will produce excellent results.

The second step comprises adding the aqueous EDDN solution to a non-aqueous, water-miscible liquid in which EDDN is not soluble, thereby crystallizing the EDDN. As with the first step, this step may take place at a temperature, pressure, and degree of agitation which produces solid EDDN within a reasonable and commercially useful period of time and at high yields.

These steps may be represented schematically by the following two step process:

Step One

Neutralization

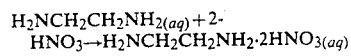

Step Two

Crystallization

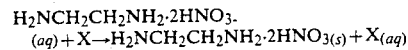

where non-aqueous liquid X is selected from ROH, RCOR', and other non-aqueous liquids. R, R' and the other non-aqueous liquids are selected to provide water miscibility of X of at least about 50 percent by weight, and provide a non-aqueous liquid X in which EDDN is insoluble. Other non-aqueous liquids include tetrahydrofuran (THF), acetonitrile, and dimethylacetamide. Methyl and ethyl alcohol are typical alcohols used, and acetone and methyl ethyl ketone are typical ketones.

The water used in the initial forming of the aqueous ethylene diamine solution should be deionized, but water from any source may be used as long as impurities do not interfere with the neutralization reaction or crystallization of the EDDN.

If nitric acid is used in the neutralization step as the acidic nitrate solution, it is commercially available as 69 to 71 weight percent $HNO_3$, depending on the particular batch purchased. As the neutralization reaction pH is quite sensitive to addition of the nitric acid as the neutral point is approached, slight changes in $HNO_3$ concentration can have large pH effects, as is more thoroughly discussed below.

The non-aqueous liquid used in the crystallization technique can be any non-aqueous liquid that meets the requirements of at least 50 percent by weight water-miscibility and non-solubility of EDDN therein. Liquids which when mixed with water form more than two phases, where EDDN solid is dispersed between more than one phase, are to be avoided, but are considered within the scope of the invention. Preferred are non-aqueous liquids which are at least 75 percent by weight miscible with water. Particularly preferred are non-aqueous liquids which are at least 95 percent by weight miscible with water. Still more particularly preferred are non-aqueous liquids which are miscible with water in all proportions. Preferred for convenience and low cost are methanol, ethanol and acetone. Methanol is the liquid of choice due to its availability and low cost. The solubility of EDDN in water/methanol and water/ethanol solutions at various temperatures are shown in Tables I and II, respectively.

TABLE I

EDDN SOLUBILITY IN WATER/METHANOL AT VARIOUS TEMPERATURES

| Wt % Water | Wt % EDDN Soluble | Temperature, °C. |
| --- | --- | --- |
| 11.1 | 0.74 | 8.5 |
| 15 | 0.5 | 0 |
| 15 | 1.0 | 9.5 |
| 15 | 1.1 | 17 |
| 15 | 1.96 | 30 |
| 15 | 2.06 | 33 |
| 15 | 3.01 | 45 |
| 15 | 4.7 | 60 |
| 17.9 | 1.9 | 22 |
| 18.4 | 4.5 | 45 |
| 20.4 | 1.8 | 15 |
| 22.3 | 4.3 | 35 |
| 25.8 | 4.1 | 28 |
| 25.0 | 2.05 | 11 |
| 29.0 | 3.9 | 21 |

TABLE II

SOLUBILITY OF EDDN IN WATER/ETHANOL AT VARIOUS TEMPERATURES

| Wt % Water | Wt % EDDN Soluble | Temperature, °C. |
| --- | --- | --- |
| 10.9 | 0.72 | 46 |
| 11.6 | 1.4 | 57 |
| 15 | 0.5 | 10 |
| 15 | 1.0 | 30 |
| 15 | 2.2 | 55 |
| 16 | 0.6 | 11 |
| 16 | 1.0 | 21 |
| 16 | 2.0 | 39 |

The neutralization reaction temperature, pressure, and degree of agitation of Step One, as stated, may be at any value which does not result in substantial vapor generation or uncontrollable temperature rise during the reaction, and yet permits the reaction to proceed to completion within a reasonable and commercially useful period of time. As is discussed further below, the temperature may be controlled in large-scale batch and continuous processes by the addition rate of nitric acid. Preferred temperature of neutralization ranges from about 0° C. to about 30° C. Lower temperatures may produce unwanted water crystals (ice) to form. Higher temperatures lead to unwanted oxidation and degradation products of the ethylenediamine reactant. Particularly preferred are neutralization reactions occurring at a temperature ranging from about 20° C. to about 30° C.

The neutralization pressure is preferably atmospheric to keep the cost of the process low. Positive and negative operating pressures would translate to design pressures and wall thicknesses for the equipment used which would be costly. However, the neutralization reaction would proceed under these conditions at substantially the same rate. Too low a pressure, combined with a high enough temperature, would result in vaporization of the aqueous ethylenediamine and lower yields, and is thus not a preferred operating mode. However, such procedures are considered within the scope of the present invention.

Agitation of the neutralization reaction vessel is necessary to provide the intimate mixing of reactants that is well known in the chemical arts. There is no preferred range of mixing or agitation rate other than that necessary to contact the aqueous ethylenediamine with the nitric acid being added to produce the desired ethylenediamine dinitrate in a reasonable and commercially useful period of time.

The pH of the neutralization reaction indicates when the neutralization reaction is complete and is therefore closely monitored. A pH ranging from about 3.0 to about 4.0 indicates complete neutralization of ethylenediamine and is therefore preferred. The pH may be measured by methods known to those skilled in the art.

Closely related to the pH of the neutralization reaction are the amount and rate of addition of nitric acid. In small batch operations, the nitric acid may be added all at once via an addition funnel, whereas in larger batch or continuous processes the nitric acid may be metered or pumped into the reaction vessel at a rate which does not result in uncontrollable temperature. In either case the mole ratio of nitric acid to ethylenediamine may be either less than, at, or greater than the stoichiometric mole ratio, ranging from about 0.5:1 to about 5:1. In small batch operations the mole ratio is preferably about stoichiometric, i.e., ranging from about 1.7:1 to about 2.3:1 ratio of nitric acid to ethylene diamine. In large batch and continuous methods the mole ratio preferred is also the stoichiometric value, however the usual procedure is to meter in the nitric acid to the reaction vessel while monitoring temperature. The pH is periodically measured by taking a 1 or 2 milliliter sample of the neutralization reaction and checking the pH with instrumentation well known in the art. A small amount of ethylenediamine may have to be added to ensure complete reaction of available nitric acid if the mole ratio of nitric acid to ethylene diamine was greater than 2:1. In a preferred embodiment of the reaction, there will remain a maximum of about 3 weight percent of nitric acid left unreacted in the solution containing EDDN to be crystallized. Particularly preferred neutralization reactions are those where there remains a maximum of about 1 weight percent nitric acid in the solution containing the EDDN to be crystallized.

Regarding the Second Step, the crystallization of EDDN in the non-aqueous water-miscible liquid, the neutralized EDDN solution is preferably added to a vessel containing the non-aqueous water-miscible liquid, although the methods of adding them both simultaneously or adding the non-aqueous water-miscible liquid to the neutralized EDDN solution are considered alternate ways of practicing the invention.

The temperature, pressure, and degree of agitation crystallization parameters are adjusted such as to produce the highest yield of crystalline EDDN. Specifically, the crystallization temperature may be any temperature which does not result in substantial vapor generation and yet produces crystalline EDDN in reasonable yield (expressed as weight percent of ethylenediamine) and within a reasonable period of time. Preferably the crystallization proceeds at a temperature ranging from about 0° C. to about 10° C., with a temperature ranging from about 2° C. to about 5° C. being particularly preferred.

The crystallization pressure is not critical, and like the neutralization reaction pressure, may be at positive or negative values, and this mode of operation is considered within the scope of the invention.

The degree of agitation of the crystallization solution containing EDDN is also not critical, the only requirement being that the agitation not be too strong to physically crush EDDN particles or cause unwanted vaporization of the solution. In a batch operation the agitation is preferably continued for a short time after the addition of the EDDN solution to the non-aqueous water-miscible liquid is complete. In a continuous process, the crystallization vessel size and addition rates of liquids are adjusted to provide a residence time for EDDN sufficient to crystallize substantially all of the EDDN.

The yield of EDDN as a weight percentage of ethylenediamine will vary considerably from ideal if, for example, the neutralization/crystallization technique is carried out under extreme conditions as discussed above, such as low pressure and high temperature, or where less than the stoichiometric ratio of nitric acid to ethylene diamine is used. Preferably, the yield ranges from about 25 percent to about 99 percent, with a yield ranging from about 75 to about 99 percent being particularly preferable, and a yield of about 95 percent being typical.

The novel process of the present invention is safer than existing procedures in that nitric acid addition is performed into an aqueous medium, thus substantially precluding the formation of the hazardous methyl and ethyl nitrates. Also, addition of the thus-formed EDDN aqueous solution to the described non-aqueous water-miscible liquid is not exothermic, thereby precluding the occurrence of a runaway reaction.

This neutralization/crystallization technique unexpectedly consistently produces EDDN with an average particle size of about 28 to about 32 microns of rounded oblong platelets. This is true even when the process is scaled up to commercial production quantities, and is preferred over EDDN of large average particle size produced in the other processes currently known in the art.

The following examples are intended to illustrate the invention and are in no way to be considered as a limitation on the inventive concept.

EXAMPLE 1

To a 3-liter, jacketed, round bottom flask with a bottom outlet and fitted with an addition funnel, stirrer, and thermometer were charged 790 grams of water and 339 grams of ethylenediamine. To this stirred solution was added, via the addition funnel, 1,006 grams of 70 weight percent $HNO_3$. The temperature was maintained between 20° C. and 30° C. by circulating ice water through the jacket as the neutralization reaction proceeded and ethylenediamine dinitrate formed. The ethylenediamine dinitrate solution was then added, via the bottom outlet, to a 12-liter, round bottom flask fitted with a cooling bath and stirrer, which contained 6,145 grams of anhydrous, denatured ethanol cooled to about 3° C. The ethylenediamine dinitrate precipitated as a white crystalline solid. The slurry was stirred for 30 minutes, filtered, and the filter cake washed with about 1,000 grams of fresh denatured, anhydrous ethanol. On drying, 897 grams (95.4 percent yield, m.p. 187°–187.5° C.) of EDDN product was obtained. The EDDN was characterized by FT-IR (Fourier transform-infrared) spectroscopy, DSC (differential scanning calorimetry), and equivalent weight determination. The average particle size of the EDDN was measured using photomicrographs of the product, and was found to be 30 microns.

The reaction was repeated five times to establish the reproducibility of the process. The data, shown in Table III, demonstrate that consistent high yield and purity are obtained. In all of the runs the average particle size was determined to be 30 microns.

TABLE III

| REPRODUCIBILITY OF ETHYLENEDIAMINE DINITRATE PREPARATION PROCESS | | | |
| --- | --- | --- | --- |
| Run | Wt. EDDN, Grams | Wt. % EDDN | Product m.p., °C. |
| 1 | 887 | 95.4 | 187–187.5 |
| 2 | 899 | 96.7 | 187–187.5 |
| 3 | 885 | 95.2 | 187–187.5 |
| 4 | 880 | 94.6 | 187–187.5 |
| 5 | 879 | 94.5 | 187–187.5 |
| 6 | 894 | 96.1 | 187–187.5 |

This process was scaled up to 100- and 200-liter glassware systems for Example 2.

EXAMPLE 2

To a 100-liter glass reactor fitted with internal cooling coils, a bottom outlet, agitation and metering pump feed system was charged 23.6 liters of deionized water and 10.2 kg of ethylenediamine. The solution was cooled to 5° C. and 30.3 kg of 70 weight percent $HNO_3$ was metered into the aqueous ethylenediamine solution. The solution temperature was maintained between 20° C. and 30° C. by adjusting the 70 weight percent $HNO_3$ feed rate. The neutralization was monitored for completion by taking a 1 mL sample for pH measurement; the measured pH was 2.3 and 50 grams of ethylenediamine was added to bring the pH to 3.1.

To an adjacent 200-liter glass vessel fitted with an agitator, bottom outlet, and a feed line from the 100-liter reactor was charged 92.6 kg of methanol. One-half the content (about 28 liters) of the aqueous ethylenediamine dinitrate solution was added to the rapidly stirred methanol, precipitating the ethylenediamine dinitrate, and stirring was continued for 30 minutes after the addition was complete. The slurry was filtered and the filter cake washed with 15 liters of fresh methanol. The product was then packaged into polyethylene bags and the material dried in a large oven.

The precipitation procedure was repeated with the remaining one-half of the ethylenediamine dinitrate solution. On drying, the combined yield for the two quench procedures was 27.9 kg (93.9%). The melting point (187°–187.5° C.), particle size, and FT-IR spectrum were the same as previously prepared material.

EXAMPLE 3

This example demonstrates the use of acetone, THF, and acetonitrile in crystallizing aqueous EDDN. In using each, a 250 mL Erlenmeyer flask was charged with acetone, THF, or acetonitrile as the case might be, and while magnetically stirring in an ice bath, aqueous EDDN (50 weight percent EDDN solution), 50 grams, was added dropwise. The EDDN used comprised a standard solution of EDDN made by dissolving 98 grams of EDDN in 98 grams of water at 25° C. to make a 50 weight percent EDDN solution.

After addition of the EDDN, the resulting thick white slurry was vacuum filtered and washed with 25 mL of acetone, THF, or acetonitrile, depending on which liquid was tested. The resulting cake was dried in a vacuum oven at 50° C. The recoveries for the various liquids tested are given in Table IV. The melting points for EDDN recovered ranged from 187.5° to 188.5° C. in each test.

TABLE IV

RECOVERIES AND MELTING POINTS OF EDDN WHEN USING VARIOUS CRYSTALLIZATION STEP LIQUIDS

| Liquid Used to Crystallize EDDN | Wt. EDDN Charged (gms) | Wt. EDDN Recovered (gms) | % EDDN Recovered |
|---|---|---|---|
| Acetone | 25 | 22.0 | 88 |
| THF | 25 | 23.0 | 92 |
| Acetonitrile* | 10.7* | 8.7* | 81 |

*Only 21.5 grams of 50 weight percent EDDN solution was used along with only 55 mL of acetonitrile The preceding examples do not exhaust the variations of use of the inventive process considered to be within the scope of the appended claims. For example, a very large scale commercial production of EDDN would probably consist of solvent recovery systems and continuous production of EDDN. Indeed, to those skilled in the art, many modifications and variations of the present invention are possible in light of the above teachings. It is therefore to be understood that the present invention may be practiced otherwise than as specifically described herein and still be within the spirit and scope of the appended claims.

What is claimed is:

1. A method of making ethylenediamine dinitrate comprising:
   (a) reacting aqueous ethylenediamine with nitric acid to form an aqueous ethylenediamine dinitrate solution substantially depleted of unreacted nitrate ions; and
   (b) combining said ethylenediamine dinitrate solution with a non-aqueous liquid, miscible with water in amounts of at least about 50 percent by weight, and in which ethylenediamine dinitrate is insoluble, to form solid ethylenediamine dinitrate.

2. A method in accordance with claim 1 in which step (a) is performed at a temperature ranging from about 0° C. to about 30° C.

3. A method in accordance with claim 2 in which step (a) is performed at a temperature ranging from about 20° C. to about 30° C.

4. A method in accordance with claim 1 in which said ethylenediamine dinitrate solution has a pH ranging from about 3.0 to about 4.0.

5. A method in accordance with claim 2 in which said ethylenediamine dinitrate solution has a pH ranging from about 3.0 to about 4.0.

6. A method in accordance with claim 1 in which said non-aqueous liquid is selected from the group consisting of methanol, ethanol, acetone, methyl ethyl ketone, tetrahydrofuran, acetonitrile, and dimethylacetamide.

7. A method in accordance with claim 6 in which said non-aqueous liquid is methanol.

8. A method in accordance with claim 6 in which said non-aqueous liquid is ethanol.

9. A method in accordance with claim 6 in which said non-aqueous liquid is acetone.

10. A method in accordance with claim 1 in which said non-aqueous liquid is miscible with water in amounts of at least about 75 percent by weight.

11. A method in accordance with claim 1 in which said non-aqueous liquid is miscible with water in amounts of at least about 95 percent by weight.

12. A method of making ethylenediamine dinitrate comprising:
    (a) reacting aqueous ethylenediamine with nitric acid to form an aqueous ethylenediamine dinitrate solution substantially depleted of unreacted nitrate ions with pH ranging from about 3.0 to about 4.0; and
    (b) combining said aqueous ethylenediamine dinitrate solution with a non-aqueous liquid, miscible with water in amounts of at least about 50 percent by weight, and in which said ethylenediamine dinitrate is insoluble, to form solid ethylenediamine dinitrate.

13. A method in accordance with claim 12 in which said non-aqueous liquid is miscible with water in amounts of at least about 75 percent by weight.

14. A method in accordance with claim 12 in which said non-aqueous liquid is miscible with water in amounts of at least about 95 percent by weight.

15. A method in accordance with claim 12 in which said non-aqueous liquid is selected from the group consisting of methanol, ethanol, acetone, methyl ethyl ketone, tetrahydrofuran, acetonitrile, and dimethylacetamide.

16. A method in accordance with claim 15 in which said non-aqueous liquid is methanol.

17. A method in accordance with claim 15 in which said non-aqueous liquid is ethanol.

18. A method in accordance with claim 15 in which said non-aqueous liquid is acetone.

19. A method in accordance with claim 12 in which step (a) is performed at a temperature ranging from about 0° C. to about 30° C.

20. A method in accordance with claim 12 in which said step (a) is performed at a temperature ranging from about 20° C. to about 30° C.

21. A method of making ethylenediamine dinitrate comprising:
    (a) dissolving ethylenediamine in water to form aqueous ethylenediamine;
    (b) combining nitric acid with said aqueous ethylenediamine in such amount as to neutralize said aqueous ethylenediamine to form an aqueous ethylenediamine dinitrate solution substantially depleted of unreacted nitrate ions, and at a rate so as to control the neutralization temperature so as to avoid substantial vapor generation and uncontrolled temperature rise;
    (c) controlling the pH of said neutralization to between about 3.0 and 4.0;
    (d) combining said aqueous ethylenediamine dinitrate with an agitated liquid selected from the group consisting of methanol, ethanol, acetone, methyl ethyl ketone, tetrahydrofuran, acetonitrile, and dimethylacetamide, at a temperature ranging from about 0° C. to about 10° C., to form solid ethylenediamine dinitrate with an average particle size ranging from about 28 to about 32 microns in diameter; and
    (e) isolating said solid ethylenediamine dinitrate from said liquid.

22. A method in accordance with claim 21 in which said neutralization temperature of step (b) ranges from about 0° C. to about 30° C.

23. A method in accordance with claim 21 in which said neutralization temperature of step (b) ranges from about 20° C. to about 30° C.

24. A method in accordance with claim 21 in which said agitated liquid is methanol.

25. A method in accordance with claim 21 in which said agitated liquid is ethanol.

26. A method in accordance with claim 21 in which said agitated liquid is acetone.

* * * * *